United States Patent [19]

Shaldon et al.

[11] Patent Number: 4,468,329
[45] Date of Patent: Aug. 28, 1984

[54] HEMOFILTRATION SYSTEM AND SAFETY SYSTEM THEREFOR

[75] Inventors: Stanley Shaldon, Montpellier, France; Claes-Ake Gullberg, Covina, Calif.; Lars-Ake Larsson, Löddeköpinge, Sweden

[73] Assignee: Gambro Lundia AB, Sweden

[21] Appl. No.: 270,492

[22] Filed: Jun. 4, 1981

[30] Foreign Application Priority Data

Jun. 27, 1980 [SE] Sweden ................................ 8004795

[51] Int. Cl.³ ............................................. B01D 31/00
[52] U.S. Cl. ...................................... 210/651; 210/85; 210/195.2; 210/259; 210/433.2
[58] Field of Search ..................... 210/259, 195.2, 96.2, 210/85, 87, 321.1, 433.2; 604/6

[56] References Cited

U.S. PATENT DOCUMENTS

| | | | |
|---|---|---|---|
| 3,579,441 | 5/1971 | Brown | 210/259 X |
| 3,774,763 | 11/1973 | Yale et al. | 210/259 X |
| 4,081,372 | 3/1978 | Atkin et al. | 210/94 |
| 4,118,315 | 10/1978 | Fletcher et al. | 210/96.2 X |
| 4,191,182 | 3/1980 | Popovich et al. | 210/195.2 X |
| 4,276,177 | 6/1981 | Smith | 210/195.2 X |

*Primary Examiner*—Frank A. Spear, Jr.
*Attorney, Agent, or Firm*—Lerner, David, Littenberg, Krumholz & Mentlik

[57] ABSTRACT

Apparatus for hemofiltration is disclosed, including a reverse osmosis module for purifying an impure supply of water, a container for adding concentrate thereto and preparing a replacement liquid, a semipermeable hemofiltration membrane filter for filtering the supply of blood and the replacement liquid in order to produce an ultrafiltrate stream and a filtered blood stream from the supply of blood and a filtrate stream from the replacement liquid so that the filtered blood and filtrate streams can be mixed and returned to the patient. An apparatus and method are also disclosed for monitoring fluid filtration in a semipermeable filtration membrane filter including a fluid inlet for supplying the fluid to the filter for contact with the semipermeable membrane to produce a filtrate therethrough, a fluid outlet for withdrawing the fluid from the filter subsequent to such contact, a filtrate outlet for withdrawal of the filtrate from the filter, a recirculation loop for returning the fluid withdrawn from the filter back to the fluid inlet, an indicator supply for adding an indicator which will not normally pass through the semipermeable membrane to the fluid in the recirculation loop, and a detector associated with the filtrate outlet for detecting the presence of the indicator in the filtrate stream.

29 Claims, 4 Drawing Figures

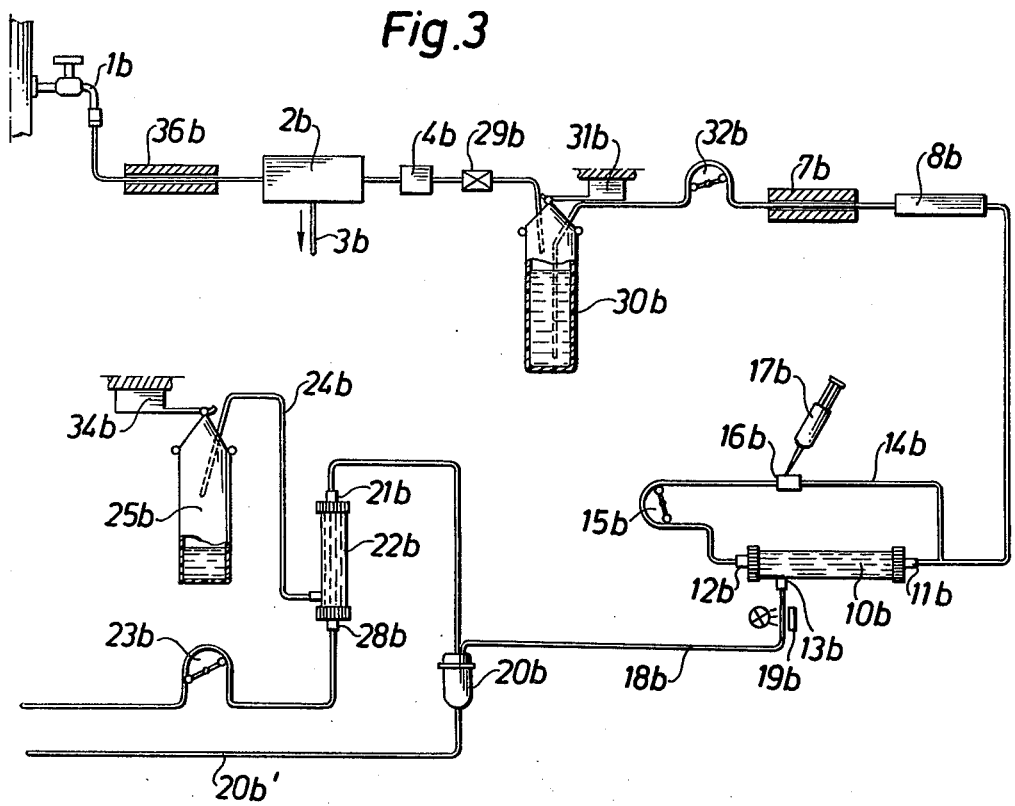
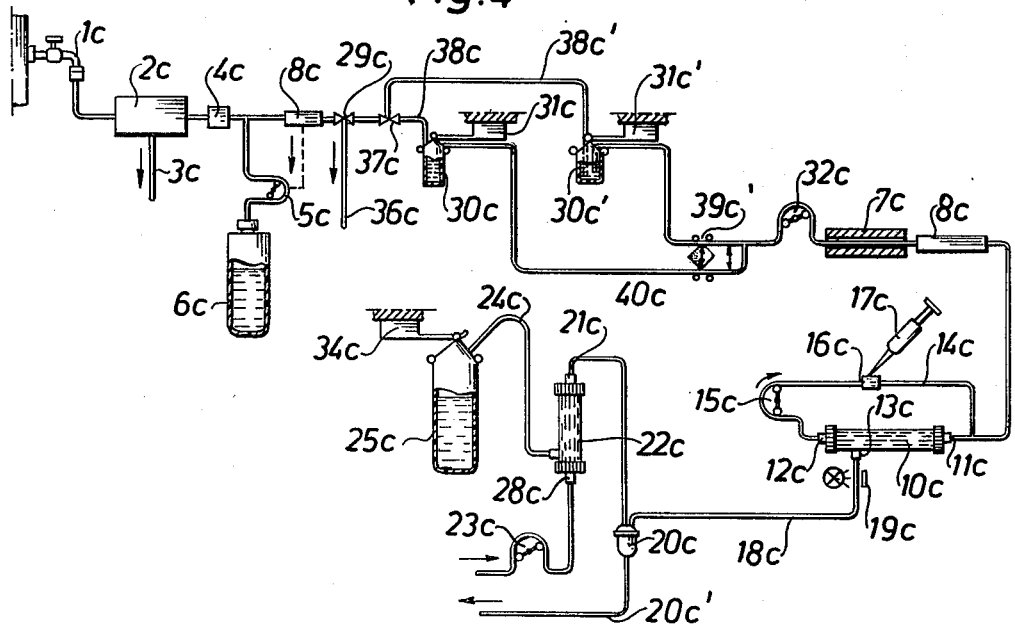

HEMOFILTRATION SYSTEM AND SAFETY SYSTEM THEREFOR

FIELD OF THE INVENTION

The present invention relates to a hemofiltration system including means for preparing an infusate solution. More particularly, the present invention relates to a safety system which is suited for use in such a hemofiltration system.

Still more particularly, the present invention relates to such a safety system used for the control or monitoring of a filter included in such a hemofiltration system, and primarily for ensuring the sterility of the infusate solution prepared in conjunction with such hemofiltration and intended to be supplied to the patient.

BACKGROUND OF THE INVENTION

During conventional hemofiltration, blood from a patient is generally passed through a hemofilter on one side of a semipermeable membrane. Through this membrane, plasma water from the blood may then be ultrafiltered. At the same time, toxic substances in the blood, such as urea, are removed. For a normal patient, the amount of ultrafiltrate is usually on the order of magnitude of 20 liters, and must therefore be replaced by a replacement of infusate solution which consists of water, to which is added suitable substances for realizing an isotonic solution.

This infusate is normally manufactured centrally in factories, and then transported to the treatment site in cans or large plastic bags containing the sterile isotonic solution. An example of the preparation of such solutions in large quantities is set forth in the article "Successful Production of Sterile Pyrogen-Free Electrolyte Solution by Ultrafiltration", Henderson et al, *Kidney International*, Vol. 14 (1978), pages 522-525.

In addition, U.S. Pat. No. 4,081,372 to Atkin et al discloses a method for detecting leaks in dialysis systems in which the hemoglobin or hemolysate is used as an indicator for leakage detection in the dialysis membrane interface.

SUMMARY OF THE INVENTION

The object of the present invention is to now provide a hemofiltration system which includes means for preparing the replacement liquid within the system itself. This system is characterized by a filter through which the prepared liquid is supplied to the patient, and under guaranteed sterile conditions.

In accordance with the present invention it has been discovered that apparatus for the hemofiltration of a supply of blood withdrawn from a patient can accomplish these results where the apparatus includes purified water supply means for purifying an impure supply of water, such as tap water, and adding concentrate thereto so as to provide a replacement liquid stream from the purified water and concentrate, filtration means for filtering the supply of blood and the replacement liquid stream comprising a semipermeable hemofiltration membrane, contact means for contacting the supply of blood and the replacement liquid stream with the filtration means to produce a filtered blood stream and an ultrafiltration stream from the supply of blood and a filtrate stream from the replacement liquid stream, and return means for returning the filtered blood stream and the filtrate stream to the patient. The purified water supply means preferably include a reverse osmosis module, and a water preheater can also be employed in association therewith, for preheating the supply of water. Preferably, the purified water supply means also includes an activated charcoal container to absorb pyrogenes and chlorine therefrom.

In accordance with a preferred embodiment of the apparatus for hemofiltration of the present invention the filter means comprises the same semipermeable hemofiltration membrane for contacting with both the supply of blood and the replacement liquid stream, and the contact means includes control means for alternately passing the supply of blood and the replacement liquid stream through the filtration means.

In accordance with another preferred embodiment of the apparatus for hemofiltration of the present invention, the filtration means comprises blood filtration means including a first semipermeable hemofiltration membrane for hemofiltration of the supply of blood and replacement liquid filtration means comprising a second semipermeable hemofiltration membrane for filtration of the replacement liquid stream.

In accordance with another embodiment of the apparatus for hemofiltration of the present invention measuring means, such as a flowmeter, are provided for measuring the amount of the ultrafiltration stream and of the replacement liquid stream produced therein.

In accordance with another embodiment of the apparatus for hemofiltration of the present invention, the return means includes mixing means, preferably a common drip chamber, for mixing the filtered blood stream with the filtrate stream.

In accordance with a preferred embodiment of the apparatus for hemofiltration of the present invention where the same semipermeable hemofiltration membrane is employed for contacting both the supply of blood and the replacement liquid stream, the contact means include a connector member which constitutes an outlet for the ultrafiltration stream produced in the filtration means and an inlet for the replacement liquid stream entering the filtration means, and the control means includes control valve means. Preferably, an ultrafiltrate receptacle is provided for collecting the ultrafiltration stream withdrawn from the filtration means through the connector member.

In accordance with another embodiment of the apparatus for hemofiltration of the present invention, the purified water supply means includes batch means for providing the replacement liquid stream in finite batches, and preferably this includes a replacement liquid container for collecting these finite batches of replacement liquid, and replacement liquid valve means for intermittently terminating the supply of replacement liquid to the replacement liquid container. In a preferred embodiment thereof, the batch means include a plurality of replacement liquid containers for collecting the finite batches of replacement liquid, and replacement liquid valve means for alternately directing the replacement liquid to each of those replacement liquid containers.

In accordance with a preferred embodiment of the apparatus for hemofiltration of the present invention in which first and second semipermeable membranes are used for each of the blood supplies and replacement liquid streams, the replacement liquid filter includes a replacement liquid inlet for supplying the replacement liquid to the replacement liquid filtration means, a filtrate outlet for withdrawing filtrate produced in the replacement liquid filtration means, a replacement liquid outlet for withdrawing the replacement liquid which does not pass through the second semipermeable membrane from the replacement liquid filtration means, and recirculation means for recirculating the replacement liquid withdrawn from the replacement liquid outlet to the replacement liquid inlet, and the recirculation means preferably includes safety means for detecting failures in the second semipermeable membrane, including indicator supply means for supplying an indicator which will not normally pass through the second semipermeable membrane to the replacement liquid in the recirculation means, and detector means associated with the filtrate outlet, the detector means being capable of detecting the presence of the indicator means in the filtrate stream. In a preferred embodiment, the recirculation means includes a recirculation pump, and the indicator supply means includes means for injecting the indicator into the replacement liquid stream, preferably a wall portion adapted for accepting a syringe therefor. Preferably, the indicator is a colorant such as blue dextrane, and the detector is photocell.

In accordance with the embodiment of the present invention in which the same semipermeable membrane is used for both the blood supply and the replacement liquid, ultrafiltration withdrawal means in fluid communication with the connector means is provided, so that when the control valve means prevents the replacement liquid from entering the filter, and the supply of blood is passing through the filter, the ultrafiltrate can be withdrawn therefrom through the ultrafiltration withdrawal means, which include a detector for detecting the presence of the filtered blood stream in the ultrafiltration stream so as to indicate failures in the semipermeable membrane. Preferably, the ultrafiltrate withdrawal means includes ultrafiltrate valve means so that the control valve means permits the replacement liquid to enter the filter, the ultrafiltration valve means can prevent movement of the ultrafiltrate through the ultrafiltrate withdrawal means.

In accordance with another embodiment of the present invention, apparatus for monitoring the filtration of a fluid by means of semipermeable filtration membrane filter is provided, including fluid inlet means for supplying the fluid to the filter so that at least a portion of the fluid can be contacted with the semipermeable membrane therein and produce a filtrate therethrough, fluid outlet means for withdrawing the fluid from the filter subsequent to that contacting with semipermeable membrane, filtrate outlet means for withdrawing the filtrate from the filter, recirculation means for recirculating the fluid withdrawn from the filter through the fluid outlet means to the fluid inlet means, indicator supply means for supplying an indicator which will not normally pass through the semipermeable membrane to the fluid in the recirculation means, and detector means associated with the filtrate outlet means and being capable of detecting the presence of the indicator means in the filtrate stream.

In accordance with a preferred embodiment of this monitoring apparatus of the present invention, the recirculation means includes a recirculation pump, and preferably the indicator supply means includes injection means for injecting the indicator into the fluid stream, preferably through a wall portion adapted to accept a syringe.

In accordance with another aspect of the present invention, a method for monitoring the filtration of a fluid by means of a semipermeable filtration membrane is provided including supplying the fluid to the filter so that at least a portion of the fluid can be contacted with the semipermeable membrane to produce a filtrate therethrough, withdrawing the fluid from the filter subsequent to contacting it with the semipermeable filtration membrane, withdrawing the filtrate produced in the filter therefrom, recirculating the fluid withdrawn from the filter for mixture with the fluid supplied to the filter, supplying an indicator which will not normally pass through the semipermeable membrane to the recirculating fluid, and detecting the presence of the indicator in the filtrate.

In accordance with the preferred embodiment of the method of the present invention the recirculating fluid is pumped back to the inlet, and preferably the supplying of the indicator comprises injecting the indicator into the recirculating fluid by means of a syringe. In a preferred embodiment, the fluid comprises a replacement fluid for use in connection with the hemofiltration of blood withdrawn from a patient, and the filtrate is intended for addition to the blood prior to its return to the patient, subsequent to hemofiltration thereof.

One of the principal concepts underlying this invention is that the system be able to include means for connection to a normal water supply conduit, and means for purifying this supplied water and mixing it with a concentrate. Preferably, the means for purifying the supplied water consists of a module for reverse osmosis. Such modules are per se known to those persons of ordinary skill in this art, and need not be described in detail. However, alternative methods of purification may also be used.

The function of the module for reverse osmosis may be improved by coupling in a preheater ahead of the module for heating the water emanating from the water supply conduit.

This means for purifying the supplied water should suitably further contain a cartridge with activated charcoal for adsorption of chlorine and pryogenes.

As is set forth in one of the above-noted preferred embodiments, a type of filter may be used which is substantially the same as those filters which are used for hemofiltration itself, i.e., a hemofilter including a semipermeable membrane. As a result, it can be assured that the filter allows the passage of desired substances, that is replacement substances, for those substances which were unnecessarily removed during hemofiltration.

Preferably, the system according to this invention includes means for measuring both the ultrafiltrate and the replacement liquid, as well as means for comparing the measured values for the purposes of calculating suitable overall weight-reduction for the patient.

The output sides of both the above-mentioned filter for the replacement liquid and the hemofiltration filter itself may suitably be connected to a common drip chamber, from which a conduit can then lead the filtrate mixture to the infusion site on the patient. In that manner, infusion is facilitated, and at the same time a simple conduit set is made possible, which is suitable for once-over use.

A particularly simple system is obtained if the hemofiltration filter itself is also used as the filter for the replacement liquid, in which case the hemofiltration filter is made operative to be driven intermittently for alternating ultrafiltration the plasma from the blood and filtration of the replacement liquid into the blood. The means for preparing the replacement liquid, in this case, may be connected to a connection socket on the hemofilter which can then also serve as an outlet or drain for the ultrafiltrate or plasma from the blood. In that case, valves are disposed alternatingly to connect the socket to the above-mentioned means for preparing the replacement liquid and to an outlet or receptacle point for ultrafiltrate removed from the blood. If batch preparation of replacement liquid is desired, the system may be provided with means for shutting down the preparation of additional replacement liquid when the desired amount of replacement liquid is available. Alternatively, the system for preparation of a certain or finite amount of replacement liquid may be disposed in a first container, and the system may be provided with means for switching the supply of replacement liquid from this first container to a second container, and vice versa, with the desired amount of liquid being found in each respective container.

Since the system according to the present invention is intended to be connected directly to a patient, it should suitably be coordinated with a safety system for control of the above-mentioned filter. The filter is thus provided, in a conventional manner, with an inlet and an outlet for the liquid which is to be filtered, and an outlet for the filtrate. This safety system is then characterized by a recirculation circuit connected to the first mentioned inlet and outlet, and includes means for the supply of an indicator which is not normally allowed through by the filter, and by a detector for the filtrate disposed after the outlet, the detector sensing if the indicator has nevertheless been allowed to pass through together with the filtrate.

The recirculation circuit should contain a recirculation pump for ensuring that the indicator is constantly caused to pass through the membrane disposed in the filter.

The indicator may, in a simple manner, be supplied to the recirculation circuit if this contains a wall portion which allows the passage of an injection syringe or the like.

As the indicator itself, a colorant, such as blue dextrane, may be used. The safety system is provided with a photocell sensing device disposed downstream from the outlet for the filtrate.

BRIEF DESCRIPTION OF THE DRAWINGS

The present invention will be described in greater detail below with reference to the accompanying drawings which illustrate four different hemofiltration systems according to the invention.

FIG. 3 shows a schematic representation of yet another hemofiltration system in accordance with the present invention, with batchwise preparation of the replacement liquid, in which when a portion has been prepared, this is continuously supplied to the patient; and FIG. 4 shows a schematic representation of yet another hemofiltration system in accordance with the present invention, with continuous preparation of replacement liquid which may be divided into portions which are then continuously supplied to the patient.

DETAILED DESCRIPTION

Figure 1:
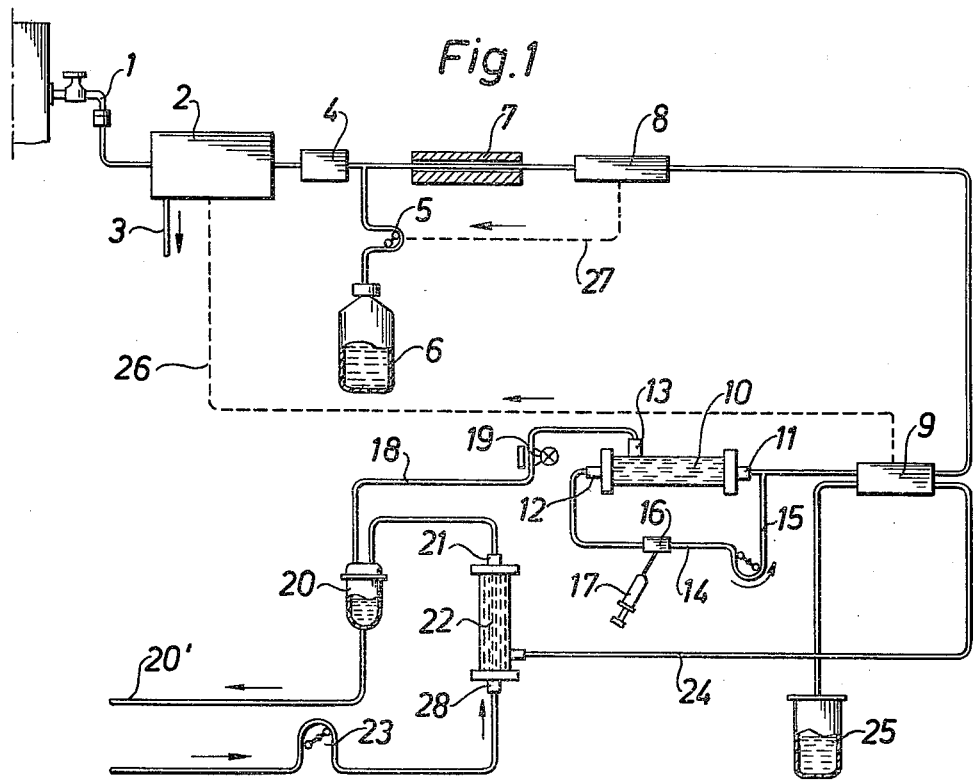
FIG. 1 shows a schematic representation of a hemofiltration system in accordance with the present invention, with continuous preparation of replacement liquid.

Referring to the figures, in which like numerals refer to like portions thereof, FIG. 1 shows a system for hemofiltration with the continuous preparation of replacement liquid. In particular, a water conduit connection, such as a normal water tap or faucet, is designated 1. The water from connection 1 is then led into a module 2 for reverse osmosis, from which waste water is drained off through conduit 3. The purified water from module 2 is passed through a container 4 which is filled with activated charcoal and is intended for adsorption of chlorine and pyrogenes. Concentrate for the replacement liquid is dosed by means of a pump 5 from a container 6 in order to realize an isotonic solution. This solution is then led through a heating device 7 and a conductivity meter 8, which in turn controls pump 5.

The prepared replacement solution is then led through a flowmeter 9 to a filter 10 with an inlet 11 and an outlet 12 for the liquid which is to be filtered, as well as an outlet 13 for the filtrate. The filter 10 may, for example, consist of a normal hemofilter containing hollow fibers of a semipermeable material.

A recirculation circuit 14 is connected to the inlet and outlets, 11 and 12, and includes a pump 15 and an injection site 16. At the injection site 16, an indicator, such as blue dextrane, may be injected into the stream by means of a normal injection syringe 17. The filtrate outlet 13 is connected to a conduit 18 which includes a photocell sensing device 19. Should a leak occur in the filter 10, this would be quickly discovered, and measures could then be taken respecting same.

Conduit 18 discharges into a drip chamber 20 to which the outlet side 21 of a hemofilter 22 is also connected. From the drip chamber 20, the mixture of replacement liquid and blood is led via conduit 20' to the patient.

The hemofilter 22 is fed by means of a pump 23 with blood from the patient (not shown). Plasma or ultrafiltrate is removed in a conventional manner through a conduit 24, through the flowmeter 9 to a receptacle site 25. The broken line 26 shows how the flowmeter 9 can be used to control the reverse osmosis module 2. In the same manner, line 27 shows how the conductivity meter 8 may be used to control the pump 5 for pumping concentrate from the container 6 to the main conduit. Finally, the blood inlet for the hemofilter 22 is designated 28.

Figure 2:
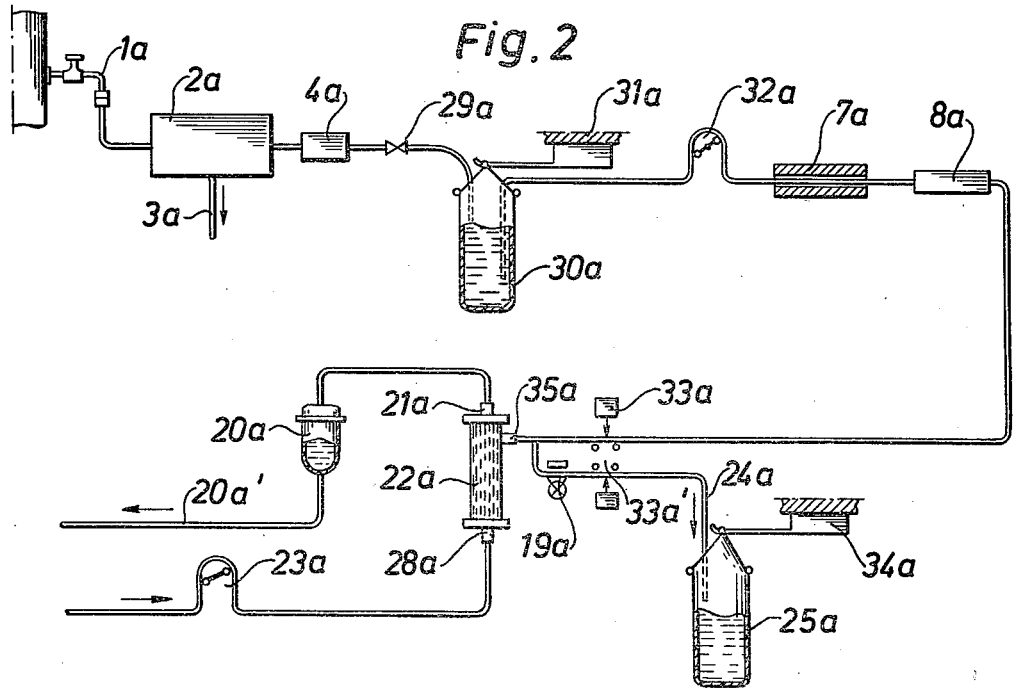
FIG. 2 shows a schematic representation of another hemofiltration system in accordance with the present invention, with intermittent preparation of replacement liquid, and with intermittent supply thereof to the patent.

The system according to FIG. 2 corresponds in essential details to that according to FIG. 1, except that in this case a system for hemofiltration is shown with the continuous preparation of replacement liquid. Corresponding details of FIG. 2 have thus been given the same reference numerals, but with the addition of an a in FIG. 2. Thus, the following list of elements applies to FIG. 2:

1a—connection point for water conduit water, such as a normal water faucet
2a—module for reverse osmosis
3a—outlet for impure water
4a—cartridge with activated charcoal
29a—shut-off valve
30a—container for replacement liquid
31a—scales for replacement liquid
32a—pump for replacement liquid
7a—heating device 8a—conductivity meter
33a—valve
33a'—valve
24a—conduit for hemofiltrate
19a—photocell sensing device
25a—receptacle container for hemofiltrate
34a—scales for hemofiltrate
22a—hemofilter
28a—blood inlet for hemofilter
21a—blood outlet for hemofilter
35a—inlet for replacement liquid and outlet for hemofiltrate
20a—drip chamber
20a'—return conduit to patient
23a—blood pump The system according to FIG. 2 differs from that in FIG. 1 in two essential respects. First, the replacement liquid is prepared batchwise in the container 30a. Here, the concentrate may either be supplied to the container initially or as desired while the process progresses. If necessary, the container may be supplemented with suitable agitator devices. When there is a suitable amount in the container 30a, valve 29a is shut off. The hemofiltration process itself may then be commenced. Here, the hemofilter 22a operates intermittently in such a manner that, for a certain period of time, such as, for example, about one minute, it works as a pure hemofilter, with valve 33a closed and valve 33a' open. These valves are then switched, and replacement liquid is supplied through the filter 22a proper by being introduced under pressure through inlet 35a. Such alternate supply of replacement liquid and ultrafiltration of the blood then continues until such time as the desired amount has been removed from the container 30a and a corresponding amount, or preferably a slightly greater amount, has been supplied to the container 25a. In the latter case, the patient will undergo a desired reduction in weight.

The system according to FIG. 3 corresponds also in essential parts to the systems according to FIGS. 1 and 2, except that in this case a system for hemofiltration is shown with the batchwise preparation of replacement liquid. Hence, the same reference numerals have also been used here, but with the addition of a b. Thus, the following list of elements applies to FIG. 3:

1b—connection point for water conduit water, such as a normal water faucet
36b—preheater
2b—module for reverse osmosis
3b—outlet for impure water
4b—cartridge with activated charcoal
29b—shut off valve
30b—container for replacement liquid
31b—scales for replacement liquid
32b—pump for replacement liquid
7b—heating device
8b—conductivity meter
10b—filter
11b—inlet for filter
12b—outlet for filter
13b—outlet for filtrate
14b—recirculation circuit
15b—recirculation pump
16b—injection site for indicator
17b—injection syringe for indicator
18b—conduit
19b—photocell sensing device
20b—drip chamber
20b'—return conduit to patient
21b—blood outlet for hemofilter
22b—hemofilter
28b—blood inlet for hemofilter
23b—pump for blood
24b—outlet conduit for the hemofiltrate
25b—receptable container for the hemofiltrate
33b—scales for the hemofiltrate The preparation of the replacement liquid according to FIG. 3 takes place in the same manner as that in FIG. 2, that is batchwise. The supply to the patient takes place, on the other hand, substantially in the same manner as in the system according to FIG. 1, that is through a filter 10b with a specially built-in safety system, and then a drip chamber 20b. The ultrafiltrate is then measured in the same manner as in the system according to FIG. 2.

The system according to FIG. 4 also corresponds in essential details to the systems according to FIGS. 1 and 3, except that in this case a system for hemofiltration is shown with the continuous batchwise preparation of replacement liquid and continuous supply to the patient. The same reference numerals have, therefore, also been used here, but with the addition of the letter c. Thus, the following list of elements applies to FIG. 4:

1c—connection point for water conduit water, such as a normal water faucet
2c—module for reverse osmosis
3c—outlet for impure water
4c—cartridge with activated charcoal
5c—pump
6c—container for concentrate
8c—conductivity meter
29c—shut off valve
36c—discharge conduit for liquid of incorrect composition
37c—valve
38c—conduit to a first dosage container
30c—first dosage container
38c'—conduit to second dosage container
30c'—second dosage container
31c—scales for first dosage container
31c'—scales for second dosage container
39c—valve
40c—valve
32c—pump for replacement liquid
7c—heating device
8c—condutivity meter
10c—filter
11c—inlet
12c—outlet
13c—outlet for the filtrate
14c—recirculation circuit
15c—recirculation pump
16c—injection site for indicator
17c—injection syringe for indicator
18c—conduit
19c—photocell sensing device
20c—drip chamber
20c'—return conduit to the patient
21c—blood outlet for hemofilter
22c—hemofilter
28c—blood inlet for the hemofiltrate
23c—blood pump
24c—outlet conduit for the hemofiltrate
25c—receptacle container for the hemofiltrate
34c—scales for the hemofiltrate The system according to FIG. 4 may be described as a combination of earlier described systems. Replacement liquid is here continuously prepared by means of details 1c, 2c, 3c, 4c, 5c, 6c and 8c. Should the conductivity be incorrect, the liquid is removed via the conduit 36c, by means of the switch valve 39c. On the other hand, if the conductivity meter 8c shows that the proper composition has been obtained, the liquid is passed via valve 37c and conduit 38c to a first dosage container 30c, which is weighed by means of scales 31c. When a suitable amount of liquid has entered this container, it can now be fed further into the system, while at the same time newly prepared liquid may be passed via valve 37c and conduit 38c to a second dosage container 30c', which is weighed by means of scales 31c'. Here, valve 39c is closed, whereas the previously prepared liquid is passed via valve 40c and pump 32c through heating device 7c and conductivity meter 8c, and via filter 10c and drip chamber 20c, to the patient. The filter 10c in this case is provided with a safety system of the above-described type. When the container 30c has been emptied, new liquid has been prepared in the container 30c'. The valves 37c, 39c and 40c may then be switched for discharge of the newly prepared liquid. During this entire period, blood is being continuously pumped by means of pump 23c through the hemofilter 22c and via drip chamber 20c back to the patient. At the same time, hemofiltrate is being removed via conduit 24c, and is collected in container 25c, which is weighed by means of scales 34c.

Naturally, the present invention is not restricted merely to the above-described examples, but may be varied within the spirit and scope of the appended claims. For example, the different details included in the systems may be varied and combined in a number of ways different from those described above. The charcoal containers 4, 4a, 4b and 4c may for instance be placed before the reverse osmosis modules 2, 2a, 2b and 2c, respectively. Before those reverse osmosis modules it is also possible to place softening devices, if the water from the tap is too hard.

What is claimed is:

1. Apparatus for hemofiltration of a supply of blood withdrawn from a patient and for the return to the patient of an infusate solution and filtered blood after hemofiltration, said apparatus comprising purified water supply means for purifying an impure supply of water provided from a source of impure water which is separate from said supply of blood and adding concentrate thereto so as to provide a replacement liquid stream comprising a purified water stream including said concentrate, the amount of said replacement liquid stream being such that substantially the entire infusate solution to be returned to the patient is derived from said replacement liquid stream; filtration means for filtering said supply of blood and said replacement liquid stream, said filtration means comprising a first semipermeable hemofiltration membrane for hemofiltration of said supply of blood and a second semipermeable membrane for filtration of said replacement liquid stream; contact means for contacting said supply of blood and said replacement liquid stream with said filtration means so as to produce a filtered blood stream and an ultrafiltration stream from said supply of blood and an infusate filtrate stream from said replacement liquid stream, said contact means including blood inlet means for supplying said supply of blood to said first semipermeable hemofiltration membrane, replacement liquid inlet means for supplying said replacement liquid stream to said second semipermeable membrane, filtered blood outlet means for withdrawing said filtered blood stream from said first semipermeable hemofiltration membrane, ultrafiltrate outlet means for withdrawing said ultrafiltration stream from said first semipermeable hemofiltration membrane, filtrate outlet means for withdrawing said infusate filtrate stream from said second semipermeable membrane, and replacement liquid outlet means for withdrawing said replacement liquid stream which does not pass through said second semipermeable membrane from said second semipermeable membrane; return means for returning said filtered blood stream and said infusate filtrate stream to said patient whereby substantially the entire infusate solution returned to said patient is derived from said replacement liquid stream; and recirculation means for recirculating said replacement liquid stream withdrawn from said replacement liquid outlet means to said replacement liquid inlet means, said recirculation means including safety means for detecting failures in said second semipermeable membrane, said safety means comprising indicator supply means for supplying an indicator which will not normally pass through said second semipermeable membrane to said replacement liquid stream in said recirculation means, and detector means associated with said filtrate outlet means, said detector means being capable of detecting the presence of said indicator in said infusate filtrate stream.

2. The apparatus of claim 1 wherein said purified water supply means includes reverse osmosis module means.

3. The apparatus of claim 2 including water preheater means associated with said reverse osmosis module means for preheating said impure supply of water.

4. The apparatus of claim 2 wherein said purified water supply means includes activated charcoal container means for contacting said impure supply of water with activated charcoal so as to absorb chlorine and pyrogenes therefrom.

5. The apparatus of claim 1 including measuring means for measuring the amount of said ultrafiltration stream and said replacement liquid stream.

6. The apparatus of claim 5 wherein said measuring means comprises a flowmeter.

7. The apparatus of claim 1 wherein said return means includes mixing means for mixing said filtered blood stream with said infusate filtrate stream.

8. The apparatus of claim 7 wherein said mixing means comprises a common drip chamber.

9. The apparatus of claim 1 wherein said purified water supply means includes batch means for providing said replacement liquid stream in finite batches.

10. The apparatus of claim 9 wherein said batch means includes replacement liquid container means for collecting said finite batches of said replacement liquid stream, and replacement liquid valve means for intermittently terminating the supply of said replacement liquid stream to said replacement liquid container.

11. The apparatus of claim 9 wherein said batch means includes a plurality of replacement liquid container means for collecting said finite batches of said replacement liquid stream, and replacement liquid valve means for alternately directing said replacement liquid stream to each of said plurality of replacement liquid container means.

12. The apparatus of claim 1 wherein said recirculation means includes recirculation pump means for pumping said replacement liquid stream withdrawn from said replacement liquid outlet means to said replacement liquid inlet means.

13. The apparatus of claim 1 wherein said indicator supply means comprises injection means for injecting said indicator into said replacement liquid stream in said recirculation means.

14. The apparatus of claim 13 wherein said injection means comprises a wall portion adapted to accept a syringe for said indicator means.

15. The apparatus of claim 1 wherein said indicator comprises a colorant, and said detector means comprises a photocell.

16. The apparatus of claim 1 wherein said second semipermeable membrane has substantially the same filtration characteristics as said first semipermeable hemofiltration membrane.

17. Apparatus for monitoring the filtration of a replacement fluid for use in connection with the hemofiltration of blood withdrawn from a patient by means of a filter comprising a semipermeable filtration membrane, said apparatus comprising replacement fluid inlet means for supplying said replacement fluid to be filtered to said filter whereby at least a portion of said replacement fluid may be contacted with said semipermeable membrane so as to produce a filtrate therethrough, replacement fluid outlet means for withdrawing said replacement fluid to be filtered from said filter subsequent to said contacting with semipermeable membrane, filtrate outlet means for withdrawing said filtrate from said filter, mixing means for mixing said filtrate with said blood withdrawn from said patient, and return means for returning said blood including said filtrate to said patient, recirculation means for recirculating said replacement fluid withdrawn from said filter through said replacement fluid outlet means to said replacement fluid inlet means, indicator supply means for supplying an indicator which will not normally pass through said semipermeable membrane to said replacement fluid in said recirculation means, and detector means associated with said filtrate outlet means, said detector means being capable of detecting the presence of said indicator in said filtrate stream.

18. The apparatus of claim 17 wherein said recirculation means includes recirculation pump means for pumping said replacement fluid from said replacement fluid outlet means to said replacement fluid inlet means.

19. The apparatus of claim 17 wherein said indicator supply means comprises injection means for injecting said indicator into said recirculation means.

20. The apparatus of claim 19 wherein said injector means comprises a wall portion adapted to accept a syringe for said indicator.

21. The apparatus of claim 17 wherein said indicator comprises a colorant, and said detector means comprises a photocell.

22. The apparatus of claim 21 wherein said colorant is blue dextrane.

23. A method for monitoring the filtration of a replacement fluid for use in connection with the hemofiltration of blood withdrawn from a patient by means of a filter comprising a semipermeable filtration membrane, said method comprising supplying said replacement fluid to said filter whereby at least a portion of said replacement fluid may be contacted with said semipermeable membrane so as to produce a filtrate therethrough, withdrawing said replacement fluid from said filter subsequent to said contacting with said semipermeable filtration membrane, withdrawing said filtrate produced in said filter therefrom, adding said filtrate to said blood withdrawn from said patient, and returning said blood including said filtrate to said patient, recirculating said replacement fluid withdrawn from said filter for mixture with said fluid supply to said filter, supplying an indicator which will not normally pass through said semipermeable membrane to said recirculating fluid, and detecting the presence of said indicator in said filtrate.

24. The method of claim 23 including pumping said recirculating fluid.

25. The method of claim 23 wherein said supplying of said indicator comprising injecting said indicator into said recirculating fluid by means of a syringe.

26. Apparatus for the hemolfiltration of a supply of blood withdrawn from a patient, said apparatus comprising purified water supply means for purifying an impure supply of water provided from a source of impure water which is separate from said supply of blood and adding concentrate thereto so as to provide a replacement liquid stream comprising a purified water stream including said concentrate, filtration means for filtering said supply of blood in said replacement liquid stream, said filtration means comprising a semipermeable hemofiltration membrane for contacting both said supply of blood and said replacement liquid stream, contact means for alternately contacting said supply of blood and said replacement liquid stream with said semipermeable hemofiltration membrane so as to alternately produce a filtered blood stream and an ultrafiltration stream from said supply of blood and a filtrate stream from said replacement liquid stream, said contact means including blood inlet means for supplying said supply of blood to said semipermeable hemofiltration membrane, connector means including ultrafiltrate withdrawal means and control valve means for alternately withdrawing said ultrafiltration stream from said semipermeable hemofiltration membrane and supplying said replacement liquid stream to said semipermeable hemofiltration membrane, whereby when said control valve means prevents said replacement liquid stream from entering said semipermeable hemofiltration membrane, said ultrafiltration stream may be withdrawn from said semipermeable hemofiltration membrane through said ultrafiltrate withdrawal means, and return means for withdrawing said filtered blood stream and said filtrate stream from said semipermeable hemofiltration membrane and returning said filtered blood stream and said filtrate stream to said patient.

27. The apparatus of claim 26, including an ultrafiltration receptacle for collecting said ultrafiltration stream withdrawn from said semipermeable hemofiltration membrane through said connector means.

28. The apparatus of claim 26, wherein said ultrafiltration withdrawal means includes detector means for detecting the presence of said filtered blood stream in said ultrafiltration stream, thereby indicating a failure in said semipermeable membrane.

29. The apparatus of claim 28, wherein said ultrafiltration withdrawal means includes ultrafiltration valve means whereby when said control valve means permits said replacement liquid stream to enter said semipermeable hemofiltration membrane said ultrafiltration valve means prevents the movement of said ultrafiltrate through said ultrafiltration withdrawal means.

* * * * *